United States Patent
Termaten

(10) Patent No.: US 6,572,616 B2
(45) Date of Patent: Jun. 3, 2003

(54) FIXING DEVICE FOR ORTHOPEDIC APPLICATIONS

(75) Inventor: Gerrit J. Termaten, Ede (NL)

(73) Assignee: Fixus B.V. (NL)

( * ) Notice: Subject to any disclaimer, the term of this patent is extended or adjusted under 35 U.S.C. 154(b) by 0 days.

(21) Appl. No.: 09/862,996

(22) Filed: May 23, 2001

(65) Prior Publication Data

US 2002/0013584 A1 Jan. 31, 2002

(30) Foreign Application Priority Data

May 24, 2000 (NL) .............................. 1015284

(51) Int. Cl.⁷ .............................................. A61B 17/64
(52) U.S. Cl. ........................................ 606/54; 606/55
(58) Field of Search ............................ 606/54, 55, 56, 606/57, 58, 59

(56) References Cited

U.S. PATENT DOCUMENTS

| | | | | |
|---|---|---|---|---|
| 2,391,537 A | * | 12/1945 | Anderson | |
| 3,977,397 A | * | 8/1976 | Kalnberz et al. | |
| 4,456,004 A | * | 6/1984 | Kenny | |
| 5,074,865 A | * | 12/1991 | Fahmy | 606/54 |
| 5,122,140 A | | 6/1992 | Asche et al. | |
| 5,207,676 A | * | 5/1993 | Canadell et al. | 606/54 |
| 5,320,622 A | | 6/1994 | Faccioli et al. | |
| 5,454,810 A | | 10/1995 | Pohl et al. | |
| 5,653,707 A | | 8/1997 | Taylor et al. | |
| 5,941,877 A | | 8/1999 | Viegas et al. | |
| 6,010,501 A | | 1/2000 | Raskin et al. | |
| 6,030,386 A | * | 2/2000 | Taylor et al. | 606/56 |
| 6,162,223 A | | 12/2000 | Orsak et al. | |
| 6,176,860 B1 | * | 1/2001 | Howard | 606/54 |
| 6,203,548 B1 | * | 3/2001 | Helland | 606/105 |
| 6,221,072 B1 | * | 4/2001 | Termaten | 606/54 |

FOREIGN PATENT DOCUMENTS

DE 43 13 767 11/1993

* cited by examiner

Primary Examiner—Ralph A. Lewis
(74) Attorney, Agent, or Firm—Larson & Taylor, PLC

(57) ABSTRACT

The invention relates to a fixing device for orthopedic applications, in which at least one coupling member is mounted in the connecting rod of, or the guiding rod for, the clamping members, intended for receiving orthopedic pins, which coupling member can be brought into a rigid or a flexible coupling position. Further, preferably it has been provided for, that in the flexible coupling position, the flexibility can be adjusted across a certain range.

7 Claims, 2 Drawing Sheets

FIXING DEVICE FOR ORTHOPEDIC APPLICATIONS

FIELD OF THE INVENTION

The invention relates to a fixing device for orthopedic applications, substantially comprising an elongated connecting rod or guiding rod, with at least two clamping members intended for clamping orthopedic pins being adjustably secured to, or being slidably mounted on said rod, and further comprising means for securing said clamping members in relation to said rod.

BACKGROUND OF THE INVENTION

Such fixing devices to be mounted externally are employed for enabling fixation of adjacent bone portions or bones at both sides of a joint in relation to each other. These devices are known in a number of embodiments, e.g. with an at least partly telescopic fastening rod having at its ends the clamping members or a guiding rod onto which said clamping members have been slidably mounted. For this last-mentioned embodiment, see e.g. NL-A-1007426 in the name of applicant.

When such fixing devices are mounted across a joint, e.g. across a wrist joint at a fracture of or near said wrist joint, this will provide the most stable situation for having the fracture heal properly. At the same time, the tendons and muscles engaging the relevant joint and the area close to it will be completely immobilized, which has the result that after the time required for healing of the fracture, generally, the joint has become completely stuck and it will often take months of physiotherapy to get the joint to move properly again.

According the aspect of the invention, in this existing method of treatment, an essential improvement can be achieved if a fixing device can also temporarily offer a possibility of movement within a certain limited range in relation to the fixing position. Due to this, it will become possible, after initial healing of the fracture, to start a treatment program in which one has a patient carry out small movements of the joint one time or a number of times a day during a certain period. In this way, the joint can be prevented from getting completely stuck and no further treatment or at least no extensive treatment will be required after the fracture has healed.

SUMMARY OF THE INVENTION

Accordingly, according to the invention it is provided for, that the connecting rod or guiding rod consists of at least two parts, a coupling member having been mounted between said parts and adjusting means having been provided by which the coupling member can be brought into a rigid coupling position or a flexible coupling position. There, the coupling member is designed in such a way that in the flexible coupling position, the parts located at both sides of the coupling member can only be changed in position across a predetermined maximum range in relation to each other. Through this, it is prevented that the healing fracture can get loaded too heavily through an excessive freedom of movement of the joint concerned.

Although one coupling member can suffice, it is preferred to mount two coupling members spaced apart on the fixing device. This has the advantage, that the fixing device, which will always be at some distance from a joint, will be more able to follow the movement of the joint within the permitted flexible range of the coupling members.

According to a further elaboration it is further provided for, that the adjusting means have been executed in such a way that with the coupling member in the flexible coupling position, the flexibility of the coupling can be controlled within a certain range. Then, the flexibility of the coupling member is preferably such, that both a flexure and a change in length is possible, which, on account of the position of the fixing device in relation to the joint concerned, is of great importance. The change in length intended can be both an extension and an reduction. The ability to control the flexibility within a certain range provides the possibility of starting the therapy with very small movements and gradually enlarging them in time, depending on the healing condition of the fracture.

Further, preferably it has been provided for that a coupling member is connected to the connecting rod or guiding rod on at least one side. This provides the possibility of mounting the coupling member(s) at a desired distance from the clamping members in front of the orthopedic pins and/or at a desired mutual distance, with the help of various lengths of connecting or guiding rod.

According to a preferred embodiment, it is provided for, that a coupling member substantially comprises a connecting part being provided with at least one helical cutout across at least a part of its length, said cut-out extending to the axis of the connecting part or a recess in the connecting part, made at the level of said axis, the adjusting means being in the shape of a retaining sleeve to be mounted across the connecting part.

According to a further elaboration, it has further been provided for, that threading is mounted on the outside of the connecting part and that the retaining sleeve is a threaded sleeve. For the type of thread to be mounted, there are a number of possibilities, such as e.g. a thread having a smaller pitch than the helical cut-out, a left- or right-hand thread or a thread incorporating the helical cut-out, such as trapezium thread.

BRIEF DESCRIPTION OF THE DRAWINGS

The invention is explained below by way of an example given in the drawing, in which.

DESCRIPTION OF THE PREFERRED EMBODIMENTS

Figure 1:
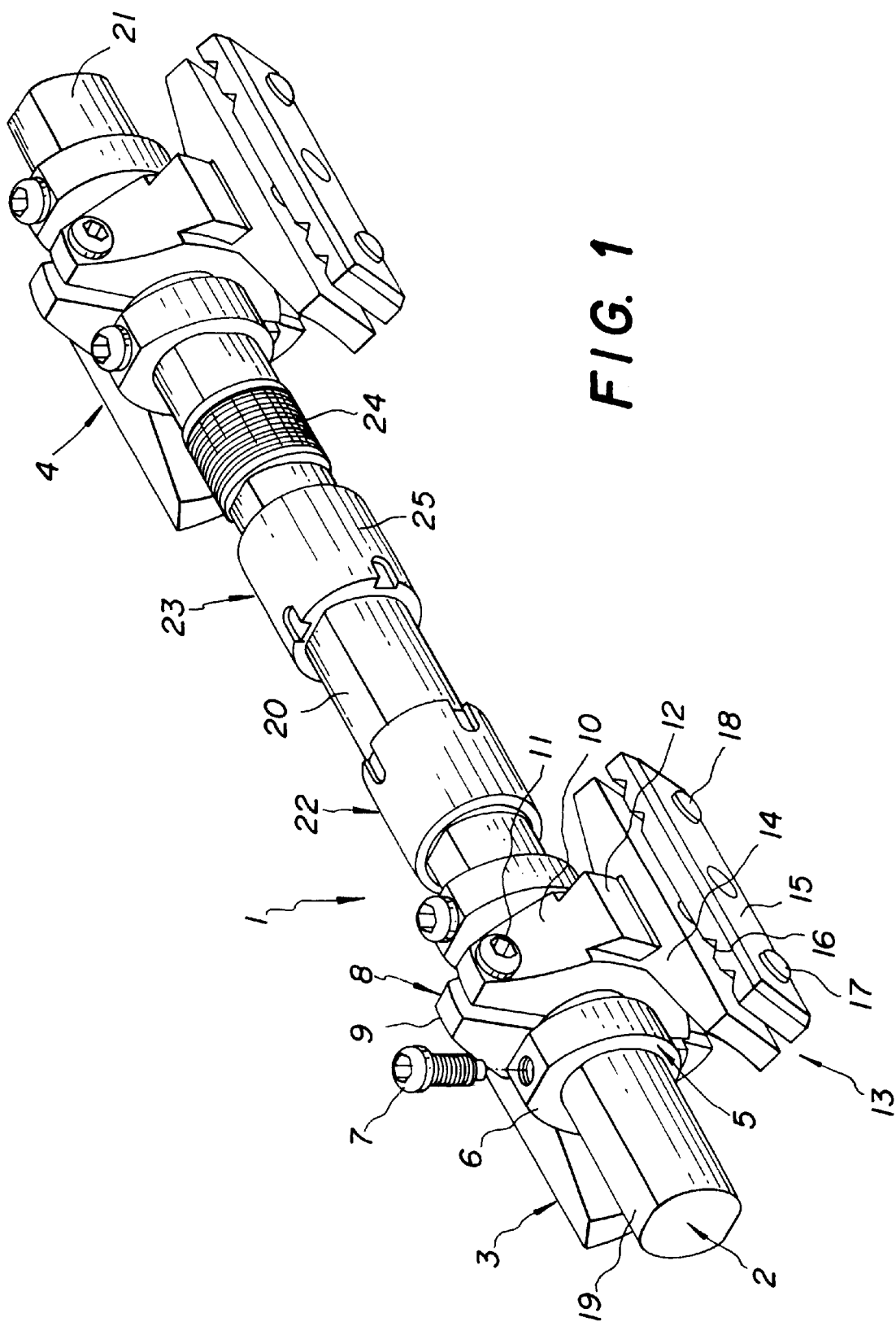
FIG. 1 shows in a perspective view a fixing device being provided with two coupling members.

Fixing device 1 shown in the example of FIG. 1 comprises a guiding rod 2 having clamping members 3, 4 mounted at both sides. A clamping member 3, 4 consists of a sliding piece 5 at both sides having a collar 6 having a securing bolt 7 by which the sliding piece 5 can he fixed onto the guiding rod 2. Sliding piece 5 is engaged by a fastening block 8 consisting of two parts 9, 10, which can be fixed on it in a desired position with clamping bolt 11. At both sides of a fastening block 8 the actual clamping means 13 for orthopedic pins not further shown in the Figure have been mounted on a guide 12. Clamping means 13 consist of a clamping bed 14 and a clamping plate 15 cooperating with it, said clamping plate 15 containing a number of grooves 16 for partly receiving orthopedic pins. Clamping plate 15 can be clamped onto the clamping bed 14 by means of bolts 17, 18, clamping one or more orthopedic pins or otherwise.

Figure 3B:
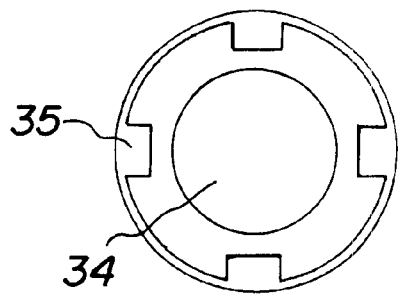
Figure 3A:
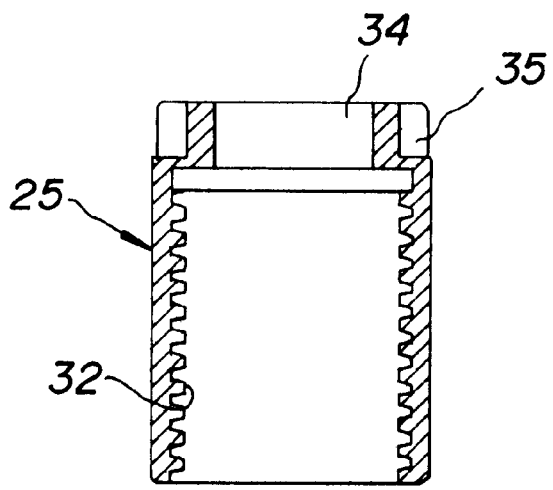

In the given Example, guiding rod 2 consists of three successive parts 19, 20, 21, between which coupling members 22, 23 have been mounted. A coupling member 22, 23 consists of a connecting portion 24 and a threaded sleeve 25 to be mounted across said connecting portion 24, see further FIGS. 2, 3.

Although the part 20 located between coupling members 22, 23 need not necessarily be a guiding rod, because no clamping member will be mounted between said coupling members, it is preferred to let it be a guiding rod, since it is made of a compound material which does not cause any disturbances in X-ray photographs.

Figure 2A:
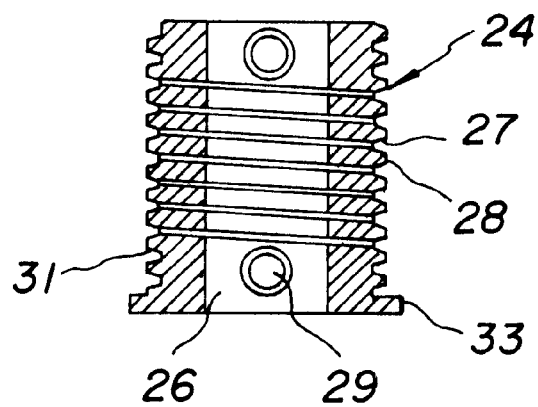
FIGS. 2A, B a connecting part of a coupling member in view and in cross-section, and FIGS. 3A, B a threaded sleeve of a coupling member in view and in cross-section.
Figure 2B:
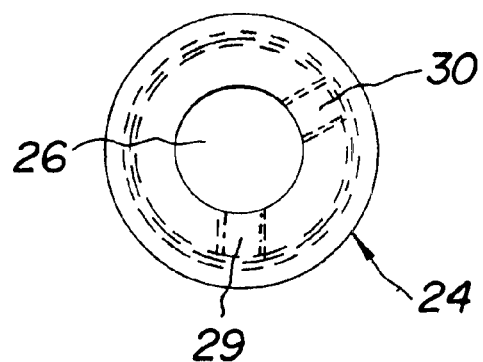

The cross-section according to FIG. 2A shows connecting part 24 being provided with a central through-bore 26 and a cut-out 27 extending across a part of the length of the connecting part 24 and extending from the outside to the central bore 26. The part 28 remaining at the level of the cut-out 27 is approximately spiral and forms, depending on the choice of material, a more or less flexible coupling in which both flexures and changes in length are possible. The cut-outs 27 make it possible that a change in length can be both an extension and a reduction.

At the ends of connecting part 24, threaded holes 29, 30 (See FIG. 2B) have been mounted, intended for receiving fastening bolts by which the connecting part can be mounted on the ends of a guiding rod. With the bore 26 and guiding rod 19, 20, 21, their ends should be screwed-off to the diameter of the bore 26.

A thread 31 is mounted on the outer side of connecting part 24, the cut-out 27 being part of said thread. In the cross-section of the sleeve 25 according to FIG. 3A, (trapezoidal) thread 32 is illustrated, which is intended to cooperate with thread 31 mounted on the outer side of connecting part 24. When screwing the sleeve 25 onto connecting part 24, an increasingly larger portion of the helical shape 28 is received within the sleeve and thereby the flexibility of connecting part 24 is increasingly reduced in order to become a rigid connection in the end when the sleeve 25 is mounted completely across the connecting part 24. There, the sleeve 25 can be fixed against the stop 33 of connecting part 24.

At the end of the sleeve 25, opposite the end where the thread 32 starts, the sleeve has an opening 34 having such a diameter that it can be located just around the guiding rod 19, 20, 21. Around the circumference, a number of hook holes 35 have been provided which are intended to be able to rotate the sleeve with a hook spanner.

What is claimed is:

1. A fixing device for orthopedic said device comprising:

an elongated rod comprising at least two parts coupled to one another by a coupling member, said coupling member comprising:

a connecting part threaded and having at least one helical cut-out across a portion of a length of said connecting part, and a threaded sleeve for threading engagement with said connecting part such that said coupling member can be brought into a rigid coupling position or a flexible coupling position;

at least two clamping members for clamping orthopedic pins adjustably displaceable on said rod; and means for securing said at least two clamping members in relation to said rod.

2. The device according to claim 1, wherein, when the coupling member is in the flexible coupling position, the flexibility of the coupling can be controlled within a certain range.

3. The device according to claim 2, wherein within said range, the coupling member provides both a flexure and a change in length between said at least two parts of said rod.

4. The device according to claim 1, wherein said coupling member has at least one end releasably connected to a portion of the rod.

5. The device according to claim 1, wherein said cut-out extends radially up to an axial through-bore of said connecting part.

6. The device according to claim 1, wherein at least a portion of the thread on the outer side of said connecting part is in the shape of a helical cut-out.

7. The device according to claim 1, wherein, around the outer circumference of said sleeve, one or more recesses are disposed for receiving a hook of a hook spanner.

* * * * *